US010265422B2

(12) United States Patent
Baranyai et al.

(10) Patent No.: US 10,265,422 B2
(45) Date of Patent: Apr. 23, 2019

(54) ETHYLENEDIAMINETETRAACETIC ACID BIS(AMIDE) DERIVATIVES AND THEIR RESPECTIVE COMPLEXES WITH MN(II) ION FOR USE AS MRI CONTRAST AGENT

(71) Applicant: BRACCO IMAGING S.P.A., Milan (IT)

(72) Inventors: Zsolt Baranyai, Debrecen (HU); Zoltán Garda, Túrricse (HU); Simona Ghiani, Almese (IT); Ferenc Krisztián Kálmán, Debrecen (HU); László Krusper, Debrecen (HU); Alessandro Maiocchi, Monza (IT); Gyula Tircsó, Debrecen (HU); Imre Toth, Debrecen (HU)

(73) Assignee: Bracco Imaging S.P.A., Milan (IT)

( * ) Notice: Subject to any disclaimer, the term of this patent is extended or adjusted under 35 U.S.C. 154(b) by 0 days.

(21) Appl. No.: 15/551,612

(22) PCT Filed: Feb. 25, 2016

(86) PCT No.: PCT/EP2016/053960
§ 371 (c)(1),
(2) Date: Aug. 17, 2017

(87) PCT Pub. No.: WO2016/135234
PCT Pub. Date: Sep. 1, 2016

(65) Prior Publication Data
US 2018/0036436 A1 Feb. 8, 2018

(30) Foreign Application Priority Data

Feb. 25, 2015 (HU) .................. 1500076
Nov. 23, 2015 (WO) ............ PCT/HU2015/000074

(51) Int. Cl.
A61K 49/10 (2006.01)
C07D 401/12 (2006.01)
C07C 237/06 (2006.01)
C07D 403/12 (2006.01)
C07D 491/107 (2006.01)
A61B 5/055 (2006.01)
C07D 207/325 (2006.01)
C07D 207/34 (2006.01)
C07D 211/16 (2006.01)
C07D 211/42 (2006.01)
C07D 211/46 (2006.01)
C07D 211/48 (2006.01)
C07D 211/62 (2006.01)
C07D 221/22 (2006.01)
C07D 295/185 (2006.01)
C07D 295/192 (2006.01)
C07D 471/08 (2006.01)
G01N 24/08 (2006.01)
G01N 33/58 (2006.01)

(52) U.S. Cl.
CPC ............ A61K 49/106 (2013.01); A61B 5/055 (2013.01); A61K 49/103 (2013.01); C07C 237/06 (2013.01); C07D 207/325 (2013.01); C07D 207/34 (2013.01); C07D 211/16 (2013.01); C07D 211/42 (2013.01); C07D 211/46 (2013.01); C07D 211/48 (2013.01); C07D 211/62 (2013.01); C07D 221/22 (2013.01); C07D 295/185 (2013.01); C07D 295/192 (2013.01); C07D 401/12 (2013.01); C07D 403/12 (2013.01); C07D 471/08 (2013.01); C07D 491/107 (2013.01); G01N 24/08 (2013.01); G01N 33/58 (2013.01); A61B 2503/40 (2013.01)

(58) Field of Classification Search
None
See application file for complete search history.

(56) References Cited

U.S. PATENT DOCUMENTS 5,316,756 A   5/1994  Gries et al.
5,419,894 A   5/1995  Gries et al.
5,693,310 A  12/1997  Gries et al.

FOREIGN PATENT DOCUMENTS

EP       130934 A1     1/1985
EP       0263059 A2    4/1988
WO   1992-21017 A1    11/1992

OTHER PUBLICATIONS

Crane, Johnathan. Inorganic Chemistry Communications 7 (2004) 107-110.*
Kalman, Ferenc K. et al., "Kinetic Inertness of the Mn2+ Complexes Formed with AAZTA and Some Open-Chain EDTA Derivatives", Inorganic Chemistry, 2012, vol. 51, No. 19, pp. 10065-10067, ACS Publications.
Naka, Kensuke et al., "Synthesis of Soluble Complexan Polymers in Organic Solvents for Using as a Polymer-Chelate Precursor to YBa2Cu3O7-x Thin Films", Bulletin of the Chemical Society of Japan, 2001, vol. 74, No. 3, pp. 571-577.
Pan, Dipanjan et al., "Manganese-based MRI contrast agents: past, present, and future", Tetrahedron, 2011, vol. 67, No. 4, pp. 8431-8444, XP028299887, ISSN: 0040-4020, DOI:10.1016/j.tet.2011.07.076.
Sosnovsky, George et al., "Spin Labeled Chelating Agents and their Gadolinium Complexes as Contrast Enhancing Agents for NMR Imaging", Z. Naturforsch, 1985, vol. 40b, pp. 1558-1562.

(Continued)

Primary Examiner — Deepak R Rao
Assistant Examiner — Laura M Daniel
(74) Attorney, Agent, or Firm — Guyan Liang

(57) ABSTRACT

The present invention relates to novel substituted ethylenediaminetetraacetic acid bisamide derivatives, their complexes with Mn(II) ion and the use thereof as contrast agents for Magnetic Resonance Imaging (MRI) analysis.

32 Claims, No Drawings

(56) References Cited

OTHER PUBLICATIONS

Sosnovsky, George et al., "Spin Labeled Bovine Serum Albumin, Spin Labeled Bovine Serum Albumin Chelating Agents and Their Gadolinium Complexes. Potential Contrast Enhancing Agents for Magnetic Resonance Imaging", Z. gaturforsch, 1986, vol. 41b, pp. 1170-1177.

Zhang, Tao et al., "Chelant extraction of heavy metals from contaminated soils using new selective EDTA derivatives", Journal of Hazardous Materials, 2013, vol. 262, pp. 464-471, Elsevier B.V.

International Search Report and Written Opinion for PCT application No. PCT/EP2016/053960, dated May 17, 2016.

\* cited by examiner

ETHYLENEDIAMINETETRAACETIC ACID BIS(AMIDE) DERIVATIVES AND THEIR RESPECTIVE COMPLEXES WITH MN(II) ION FOR USE AS MRI CONTRAST AGENT

CROSS-REFERENCE TO RELATED APPLICATIONS

This application is the national stage of corresponding international application PCT/EP2016/053960, filed Feb. 25, 2016, which claims priority to and the benefit of both Hungarian Application No. P1500076, filed Feb. 25, 2015, and international application number PCT/HU2015/000074, filed Nov. 23, 2015, all of which are hereby incorporated by reference in their entirety.

FIELD OF THE INVENTION

The present invention relates to the field of diagnostic imaging and to novel contrast agents possessing improved kinetic inertness. More in particular, it relates to novel substituted ethylenediaminetetraacetic acid bisamide derivatives, their preparation and their applications as potential ligands for preparation of Mn(II)-based MRI contrast agents.

STATE OF THE ART

Magnetic Resonance Imaging (MRI) is a renowned diagnostic imaging technique increasingly used in clinical diagnostics for a growing number of indications.

In MRI the contrast is basically due to differences existing in the longitudinal T1 and the transverse T2 relaxation times of the water protons in the different body organs and tissues, which allows the in-vivo acquisition of high-resolution, three-dimensional images of the distribution of water.

The intensity of the signal recorded in MRI stems, essentially, from the local value of the longitudinal relaxation rate 1/T1, and the transverse rate, 1/T2 of water protons, and increases with increasing of the 1/T1 value (of the longitudinal relaxation rate of water protons) while decreases with the increase of 1/T2. In other words, the shorter is T1, the higher is the intensity of the recorded signal in MRI, the better is the diagnostic image.

The strong expansion of medical MRI has further benefited from the development of a class of compounds, the MRI contrast agents, that act by causing a dramatic variation of nearby water proton relaxation rates in the tissues/organs/fluids wherein they distributes, thus adding relevant physiological information to the impressive anatomical resolution commonly obtained in the uncontrasted MRI images.

Most contrast agents used in the clinical practice are complexes of paramagnetic Gd(III) ion formed with different ligands. While these contrast agents are widely used in the diagnostic field, it may be desirable to have contrast agents based on endogenous metal ions.

Among the possible Gd(III) ion substitutes, the Mn(II) cation has a great potential since it is an endogenous metal ion, which is thus better tolerated by living systems and biological organisms (as they have an efficient route to control its homeostasis). A commercial contrast agent used in MRI containing Mn(II) ion as paramagnetic center is the so-called Mangafodipir (Teslascan, no longer available on the EU market).

Mangafodipir can be used in the diagnostics of the liver thanks to the different Mn(II) uptake of the healthy and abnormal liver cells. In the case of Mangafodipir, the Mn(II) ions released after the dissociation of the complex are absorbed because of the low kinetic inertness of the complex. Even though the manganese is an essential element, its release has to be controlled in living systems and kept at the lowest level as possible because the overexposure to Mn(II) results in its accumulation in the brain leading to neurotoxicity with Parkinson-like symptoms. For this reason, it is highly desired to use non-dissociating Mn(II) complexes as contrast agents.

Therefore, in order to be considered as a potentially valuable MRI contrast agent, a Mn(II) complex shall display a high thermodynamic, and possibly kinetic, stability ensuring against the release of toxic metal ion.

Contrast agents containing Mn(II) ion and exhibiting high kinetic stability against the release of toxic metal ion are known in the art. For instance, the U.S. Pat. No. 5,419,894, and 5,693,310 describe CDTA (trans-1,2-diaminocyclohexane-N,N,N',N'-tetraacetic acid)-bisamide derivatives and their Mn(II) complexes.

The applicant has now found a new group of CDTA-bisamides ligands which forms uncharged complexes with the Mn(II) ion having good thermodynamic stability and high kinetic inertness for the in vivo application.

SUMMARY OF THE INVENTION

An aspect of the invention relates to novel substituted ethylenediaminetetraacetic acid bisamide derivatives of general formula I, or a pharmaceutical acceptable salt thereof:

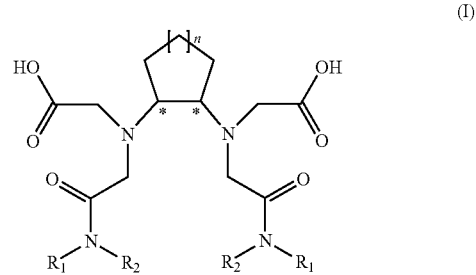

(I)

wherein:

n is 1, 2 or 3; and $R_1$ and $R_2$ are alkyl groups and at least one of them is substituted by a carboxyl group; or $R_1$ and $R_2$, taken together with the adjacent N atom, form a 5-6 membered unsubstituted aromatic ring; or $R_1$ and $R_2$, taken together with the adjacent N atom, form a 6-7 membered unsubstituted saturated ring; or $R_1$ and $R_2$, taken together with the adjacent N atom, form a 5-7 membered saturated ring substituted (i) by one or more hydroxyl and one additional moiety selected from: alkyl, hydroxyalkyl, cycloalkyl-alkyl; or (ii) by one moiety selected from: acyl, carbamoyl substituted at the carbamoyl nitrogen by one polyhydroxyalkyl, Ar, —Y—Ar, wherein Y is a moiety selected from alkyl, acyl, carbamoyl and Ar is aryl optionally substituted; or $R_1$ and $R_2$, taken together with the adjacent N atom, form a 6 membered heterocycloalkyl ring substituted at the heteroatom by —Y—Ar where Y and Ar are as defined above; or $R_1$ and $R_2$, taken together with the adjacent N atom, form a 8-11 membered satured bicyclic ring, optionally containing an heteroatom and optionally substituted.

The compounds of the above formula (I) may have two asymmetric carbon atom (marked with asterisks "*" in formula I), otherwise referred to as chiral carbon atoms, and may thus give rise to diastereoisomers and optical isomers. Unless otherwise provided, the present invention further includes all such possible diastereoisomers as well as their racemic mixtures, their substantially pure resolved enantiomers, all possible geometric isomers, and pharmaceutical acceptable salts thereof.

According to another aspect, the invention refers to respective complexes of substituted ethylenediaminetetraacetic acid bisamide derivatives of the general formula I with a Mn(II) ion or physiologically acceptable salts thereof.

A further aspect of the invention relates to the use of such complexes as contrast agents, in particular for the diagnostic imaging of a human or animal body organ or tissue by use of the MRI technique.

In a further aspect the invention relates to a manufacturing process for the preparation of the provided ligands, their complex compounds with a Mn(II) ion, or physiologically acceptable salts thereof and their use in the preparation of a diagnostic agent.

The invention further relates to a pharmaceutically acceptable composition comprising at least one Mn(II) complex compound of the invention, or a pharmaceutical salt thereof, in admixture with one or more physiologically acceptable carriers or excipients. Said compositions are useful in particular as MRI contrast media, to provide diagnostically useful images of human or animal body organs or tissues.

Therefore, in another aspect, the present invention refers to a method for the diagnostic imaging of a body organ, tissue or region by use of MRI technique that comprises the use of an effective dose of a compound of the invention.

DETAILED DESCRIPTION OF THE INVENTION

In the present description, and unless otherwise provided, the term "alkyl" comprises within its meanings a linear or branched chain comprising carbon atoms.

The term "acyl" comprises within its meanings a linear or branched chain comprising a double bonded oxygen atom and an alkyl group.

The term "hydroxyalkyl" comprises within its meanings any of the corresponding alkyl chain wherein one hydrogen atom is replaced by hydroxyl groups.

The term "polyhydroxyalkyl" comprises within its meanings any of the corresponding alkyl chain wherein more than one hydrogen atom is replaced by hydroxyl groups.

The term "aryl" refers to an aromatic hydrocarbon and, preferably, a phenyl ring.

The term "cycloalkyl ring" as used herein refers to a cycloaliphatic ring, and, preferably, a $C_5$-$C_7$ carbocyclic ring e.g. a cyclopentyl ring.

The term "heterocycloalkyl ring" comprises within its meanings a satured heterocycle having 2 equal or different heteroatoms in the cyclic chain.

The term "bicyclic ring" as used herein refers to a molecule that features two rings. The joining of the rings can occur through an unbranched chain of atoms that connects two carbon atoms of a ring, as in bridged compounds, or through a single atom shared by the two rings, as in spiro compounds.

From all the above, having defined the meanings for alkyl and aryl, any composite-name such as cycloalkyl-alkyl and the like should be clear to a skilled person.

Just as an example, and unless otherwise provided, the term cycloalkyl-alkyl comprises within its meanings an alkyl further substituted by a cycloalkyl (e.g. cyclopentyl-methyl=$C_5H_{11}$—$CH_3$—).

The term "pharmaceutically acceptable salt", as used herein, refers to derivatives of the compounds of the invention wherein the parent compound is suitably modified by converting any of the free acid or basic groups, if present, into the corresponding addition salt with any base or acid conventionally intended as being pharmaceutically acceptable.

The term "effective amount" or "effective dose", as used herein, refers to any amount of a paramagnetic chelated complex of the formula (I) according to the invention or pharmaceutical composition thereof, that is sufficient to fulfil its intended diagnostic purpose(s): i.e., for example, to ex vivo visualize a biological element including cells, biological fluids and biological tissues or the in vivo diagnostic imaging of body organs, tissues or regions of a patient.

Unless otherwise indicated, with "individual patient" or "patient" as used herein we refer to a living human or animal patient, and, preferably a human being undergoing MR diagnostic assessment.

DESCRIPTION OF THE INVENTION

In a first aspect, the invention relates to substituted ethylenediaminetetraacetic acid bisamide derivatives of the general formula I, or a pharmaceutical acceptable salt thereof:

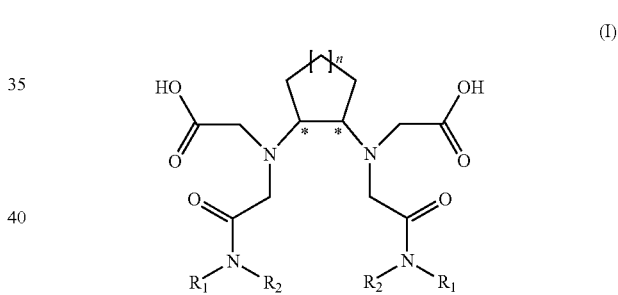

(I)

wherein n, $R_1$ and $R_2$ are as defined above.

In one embodiment, the invention relates to compounds of formula (I) in which n is preferably 2.

In another embodiment, the invention relates to compounds of formula (I) in which $R_1$ and $R_2$ are alkyl groups and at least one, preferably just one, of them is substituted by a carboxy group.

In another embodiment, $R_1$ and $R_2$ in the above formula (I), taken together with the adjacent N atom, form a 5-6 membered, preferably 5 membered, unsubstituted aromatic ring.

In an alternative embodiment, $R_1$ and $R_2$ in the above formula (I), taken together with the adjacent N atom, form a 6-7 membered unsubstituted saturated ring.

In an alternative embodiment, in the above formula (I) $R_1$ and $R_2$, taken together with the adjacent N atom, form a 5-7 membered, preferably 6 membered, saturated ring substituted by one or more, preferably one, hydroxyl and one additional moiety selected from: alkyl, hydroxyalkyl, cycloalkyl-alkyl, preferably methyl, hydroxymethyl, cyclopentylmethylene or cyclohexylmethylene.

Preferably, the hydroxyl moiety is in the meta or para position with respect to the N atom, methyl or hydroxymethyl moieties are in the orto or meta position, and cyclopentylmethylene or cyclohexylmethylene moieties are in the para position.

If the additional moiety is a methyl or hydroxymethyl in the orto position, the hydroxyl moiety on the saturated ring is more preferably in the meta position. If the additional moiety is a methyl or hydroxymethyl in the meta position, the hydroxyl moiety on the saturated ring is more preferably in the meta or para position.

If the additional moiety is a cyclopentylmethylene or cyclohexylmethylene, the hydroxyl moiety on the saturated ring is more preferably in the para position.

In one additional embodiment, $R_1$ and $R_2$ in the above formula (I), taken together with the adjacent N atom, form a 5-7 membered, preferably 5-6 membered, saturated ring substituted by acyl, preferably carboxyl.

Preferably, the saturated ring is substituted by carboxyl in the meta or para position, more preferably in the para position.

In another embodiment, $R_1$ and $R_2$ in the above formula (I), taken together with the adjacent N atom, form a 5-7 membered, preferably 6 membered, saturated ring substituted by a aminocarbonyl moiety which is in turn substituted at the aminocarbonyl nitrogen by one polyhydroxyalkyl, preferably bis(hydroxymethyl)methyl [—CH(CH$_2$OH)$_2$], 2,3,4,5,6-hydroxyhexyl [—CH$_2$—CH(OH)—CH(OH)—CH(OH)—CH(OH)—CH$_2$(OH)], or, more preferably, 2,3-hydroxypropyl [—CH$_2$—CH(OH)—CH$_2$(OH)].

Preferably, the saturated ring is substituted in the para position.

In another embodiment, $R_1$ and $R_2$ in the above formula (I), taken together with the adjacent N atom, form a 5-7 membered, preferably 6 membered, saturated ring substituted by Ar or by —Y—Ar wherein Y is preferably methylene (—CH$_2$—), carbonyl (—CO—), aminocarbonyl (—CO—NH—) and Ar is preferably phenyl.

If the saturated ring is substituted by Ar or by —Y—Ar wherein Y is methylene, the phenyl residue is preferably unsubstituted or substituted by one or two hydroxyl or by one moiety selected from nitro, amino, sulphonic, hydroxyalkyl, more preferably hydroxymethyl. Preferably, the saturated ring is substituted in the para position by phenyl or phenylmethylene wherein the phenyl residue is unsubstituted or substituted by two hydroxyl moieties in the orto positions or by one moiety selected from nitro, amino, sulphonic, hydroxymethyl in the para position.

If Y is carbonyl, the phenyl residue is preferably substituted by one or two hydroxyl. Preferably, the saturated ring is substituted in the para position by phenylcarboxy, wherein the phenyl residue is substituted by one hydroxyl moiety in the para position.

If Y is aminocarbonyl, the phenyl residue is preferably substituted by one or two hydroxyl or by one hydroxyalkyl. Preferably, the saturated ring is substituted in the orto or para position, more preferably in the para position, by a phenylaminocarbonyl residue, wherein the phenyl residue is further substituted by two hydroxyl moieties, one in the orto and the other in the para position (with respect to the C linked to the aminocarbonyl group) or, more preferably, both in the orto positions, or by one hydroxyl or hydroxyalkyl in the para position.

In one additional embodiment, $R_1$ and $R_2$ in the above formula (I), taken together with the adjacent N atom, form a 6 membered heterocycloalkyl ring comprising a second heteroatom, preferably N, said second heteroatom being substituted by a sulphonic group or by —Y—Ar wherein Y is preferably carbonyl and Ar is preferably phenyl substituted by one or, preferably, two hydroxyl moieties. Preferably, the second heteroatom on said 6 membered heterocycloalkyl ring is in the para position with respect to the N atom. Preferably, the second heteroatom is substituted by a carbonylphenyl residue, wherein the phenyl is in turn substituted by two hydroxyl moieties, one in the orto and the other in the para position or, more preferably, both in the orto positions.

In an alternative embodiment, $R_1$ and $R_2$ in the above formula (I), taken together with the adjacent N atom, form a 10- or 11-membered spiro ring, preferably containing an additional heteroatom, preferably O, and preferably substituted by one hydroxyl, preferably in the para position. In a further embodiment, $R_1$ and $R_2$ in the above formula (I), taken together with the adjacent N atom, form an 8-membered bridged ring, preferably substituted by one or two hydroxyl, more preferably one, preferably in the para position.

The following are preferred examples of compounds of formula (I):

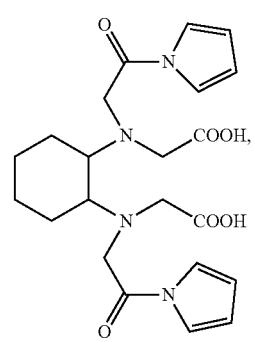

Compound 1

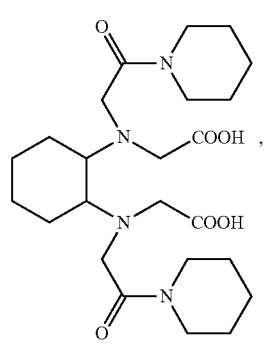

Compound 2

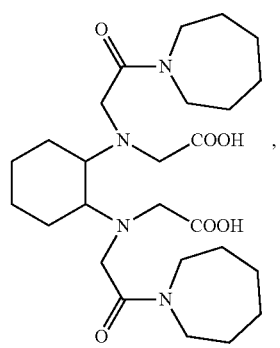

Compound 3

Compound 4
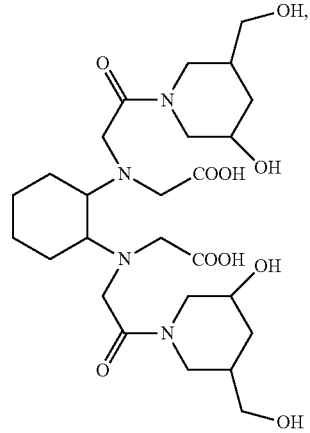
Compound 5
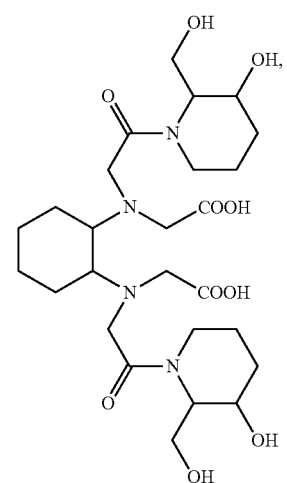
Compound 6
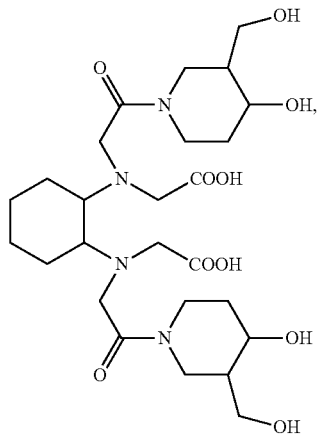
Compound 7
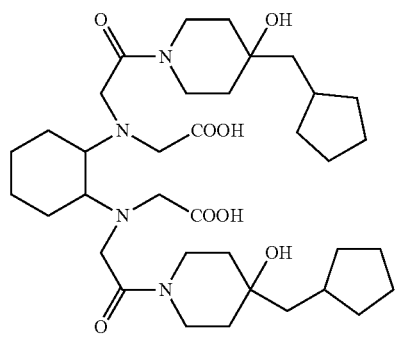
Compound 8
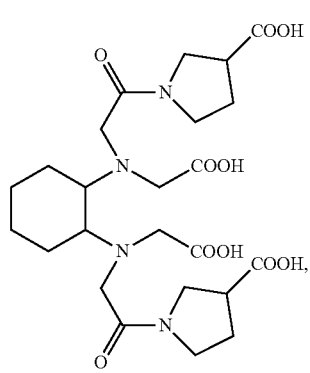
Compound 9
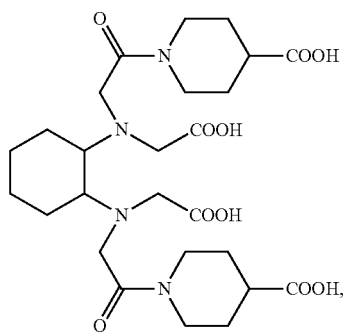
Compound 10
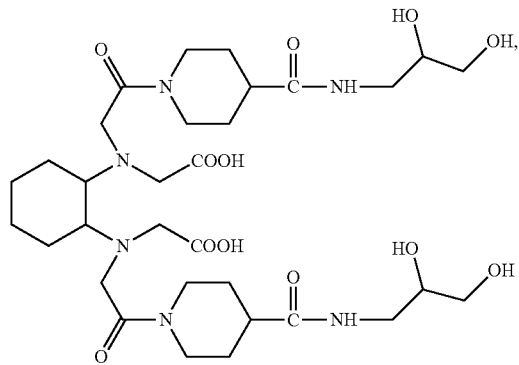

Compound 11
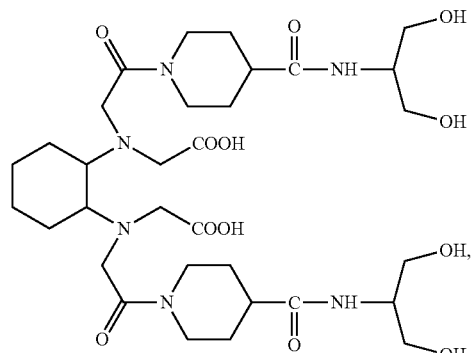

Compound 12
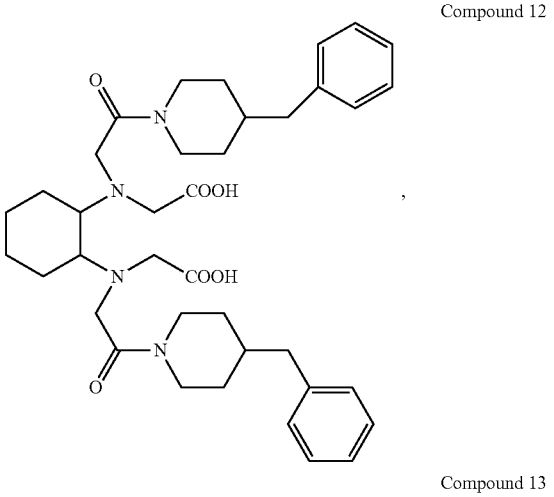

Compound 13
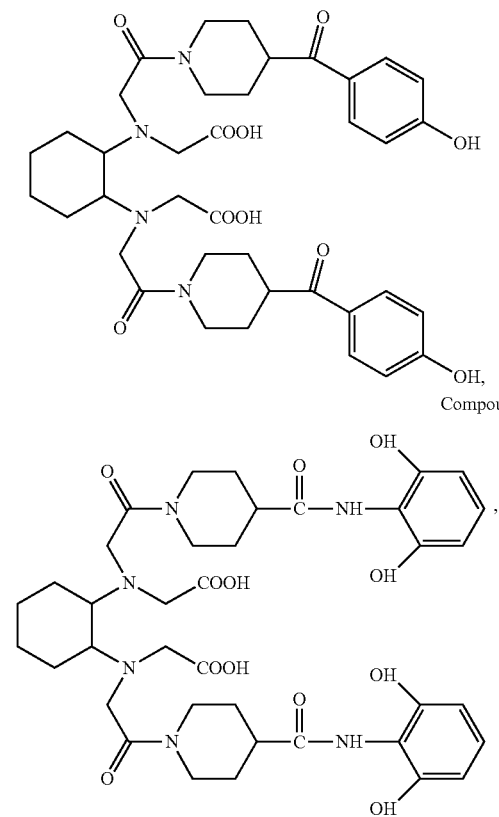

Compound 14

Compound 15
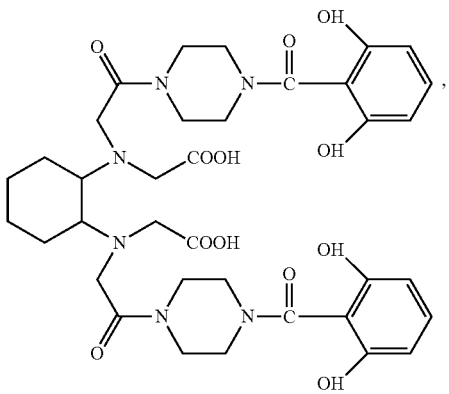

Compound 16
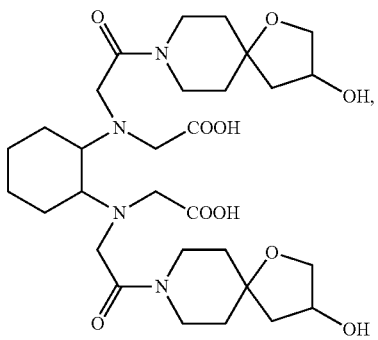

Compound 17

Compound 18
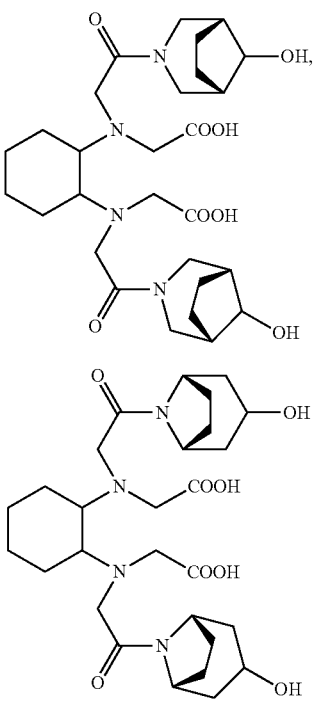

According to another aspect, the invention refers to the respective complexes of the compounds of formula I as above illustrated with a Mn(II) ion or physiologically acceptable salts thereof.

In certain embodiments the R,S diastereoisomeric form is particularly preferred, e.g. for the Mn(II) complexes of Compound 2, Compound 9 and Compound 12.

The present Mn(II) complexes or pharmaceutically acceptable salts thereof are suitable for the use as MRI contrast agent.

Therefore, in a further aspect, the invention relates to the use of the compounds of formula (I) in the form of Mn(II) complex, or a pharmaceutical acceptable salt thereof, as contrast agents, in particular for the diagnostic imaging of a human or animal body organ or tissue by use of the MRI technique.

In a further aspect the invention relates to a manufacturing process for the preparation of the compound of formula I, their complex compounds with a Mn(II) ion, or physiologically acceptable salts thereof and their use in the preparation of a diagnostic agent.

Compounds of formula (I), and the Mn(II) complexes thereof, may be prepared through a general synthetic process comprising the following steps:
  a) synthesis of CDTA-dianhydride;
  b) opening reaction of the CDTA-dianhydride in the presence of a secondary amine to give the corresponding bisamide;
  c) complexation of the obtained bisamide with a Mn(II) ion and isolation of the Mn(II) complex, or the salt thereof;

In the case the secondary amine is not commercially available, it may be synthesized in an intermediate step between a) and b), according to procedures known to those skilled in the relevant art, for instance by simple coupling reaction between amine and carboxylic acid adding protective groups.

Optionally, a HPLC separation of the racemic mixture may be performed either before or after the complexation of Mn(II) with the compound of formula I. If before complexation, a chiral column has to be used; if after complexation, a standard HPLC column (such as a preparative column C18 RP) may be advantageously used.

The single steps of the above general process, comprehensive of any variant thereof, may be carried out according to conventional methods known in the art.

The CDTA-dianhydride may be obtained as disclosed for instance in these publications: G. Sosnovsky, S. W. Li, R. N. U. Maheswara, Z. Naturforsch. (1985), 40b, 1558-62; G. Sosnovsky, R., N. U. Maheswara, J. Lukszo, R. C. Brasch, Zeitschrift fuer Naturforschung, Teil B: Anorganische Chemie, Organische Chemie (1986), 41B(9), 1170-7; N. Kensuke, T. Yasuyuki, Y. Kunitoshi, O. Akira, C. Yoshiki, M. Shigeru, Bulletin of the Chemical Society of Japan (2001), 74(3), 571-577.

The opening reaction of the CDTA-dianhydride to give the corresponding bisamide may be obtained as disclosed for instance in this publication: T. Zhang, J.-M. Liu, X.-F. Huang, B. Xia, C.-Y. Su, G.-F. Luo, Y.-W. Xu, Y.-X. Wu, Z.-W. Mao, R.-L. Qiu, Journal of Hazardous Materials (2013), 262, 464-471.

The complexation of the compounds of formula (I) e.g. with a Mn(II) ion may be performed, for instance, by stoichiometric addition of a suitable Mn(II) derivative, particularly a Mn(II) salt (e.g. $MnCl_2$), or oxide (e.g. MnO), to a solution of the ligand (e.g. water), by working according to well-known experimental methods.

Finally, any of the free acidic groups (e.g. carboxylic) of the complex may be optionally converted into a corresponding pharmaceutically acceptable salt. The operative conditions for the optional salification of the compounds of the invention are within the ordinary knowledge of the skilled person.

An exemplificative implementation of the above general procedure leading to the compounds of the formula (I) and of the Mn(II) complexes thereof, is schematized in the following Scheme:

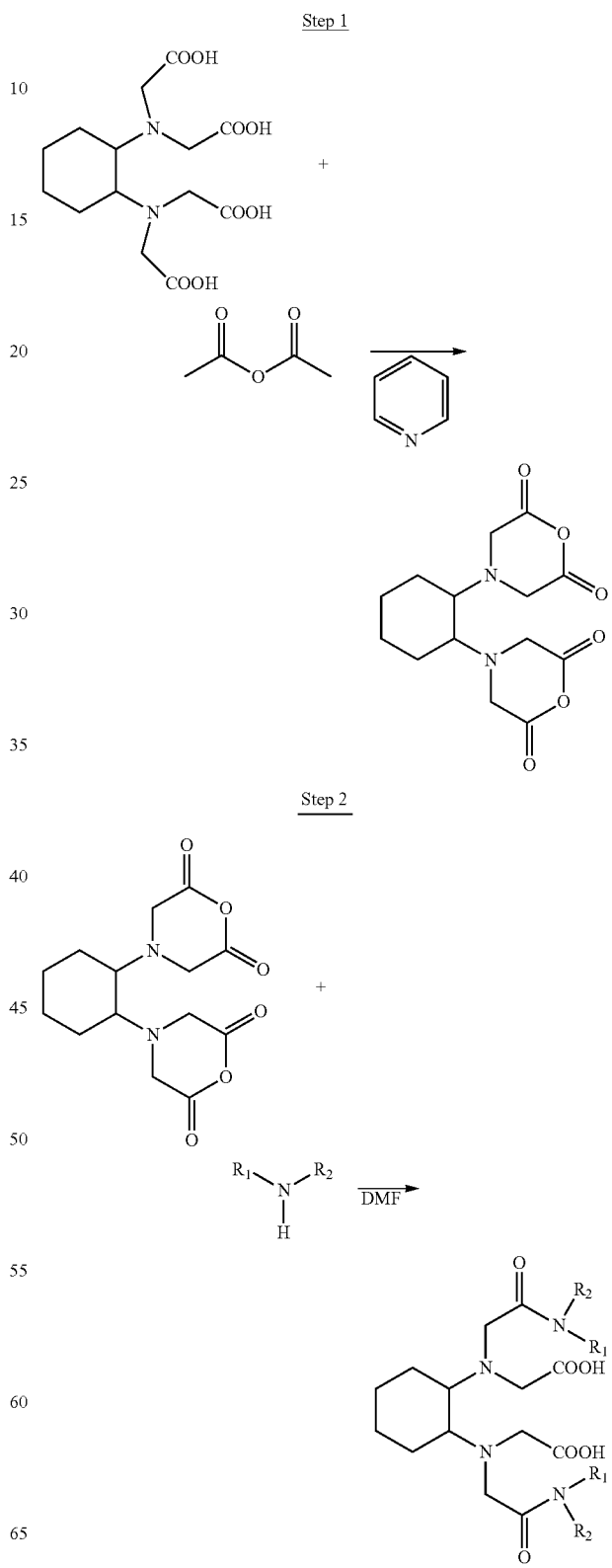

-continued

Step 3

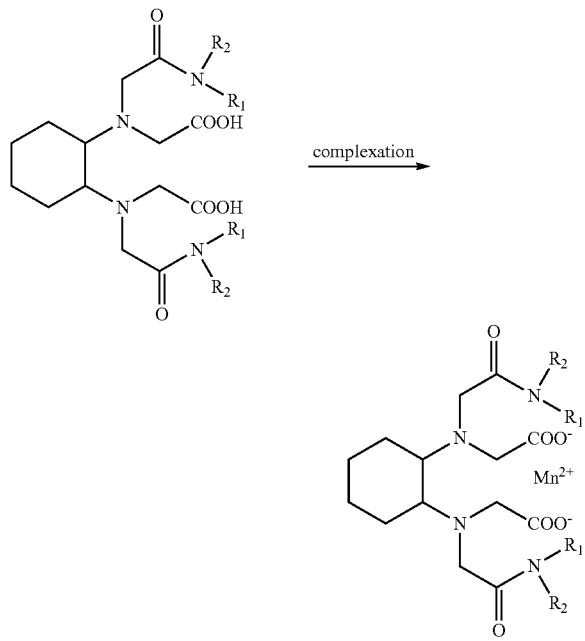

in which, in the first step, CDTA is reacted with acetic anhydride (preferably in the presence of acetic anhydride and pyridine) to give the corresponding cyclic dianhydride. In the second step, CDTA-dianhydride is reacted with a secondary amine (preferably in dry DMF) to give the corresponding bisamide. In the third step, the CDTA-bisamide derivative is complexed with the Mn(II) ion to give the desired Mn(II) complex of formula (I).

Specific examples of preparation of preferred compounds of formula (I) according to the invention are moreover provided in the following experimental section, constituting a general reference to the operative conditions being employed in the above processes.

Although not willing to be bound by any particular theory, the Applicant considers that the kinetic inertness of the Mn(II) complexes of the compounds of formula (I) may be significantly improved as a result of the combined effect promoted by these peculiar structural components. In particular, it may be hypothesized that the rigid structure of the ligands of the present invention ensures a relatively high kinetic inertness, which results in a negligible decomplexation of the Mn(II) ion. More in particular, it is hypothesized that the 6 membered saturated ring of CDTA and/or the tertiary N atoms of the amides provide a surprising stability to the complexes of the invention. In view of the improved kinetic inertness values of the compounds of the invention, the possible release of the metal ion from the complex is strongly impaired or substantially avoided. For instance, as inferable from the experimental data, the percentage of the decomplexation related to the total injected amount lies between 0.3-3%, while the half-life (measured at 25° C. and pH=7.4) reaches the value of 984 hours.

Furthermore, as shown in the Experimental part, the relaxivity values of the Mn(II) complexes of the invention are comparable to the relaxivity values of known Gd(III)-based compounds.

These results render the Mn(II) complex compounds of the invention suitable as Non Specific contrast agents, i.e. as MRI contrast agents suitable for a general use, similar to the contrast agents of the market like Dotarem®, ProHance® and Magnevist®.

Mn(II) complexes of the compounds of formula (I), or the pharmaceutical acceptable salt thereof, thus find advantageous use in the preparation of pharmaceutical formulations intended for a general use in the diagnostic imaging of a human or animal body organ, tissue or region either in vivo or in vitro, ex vivo.

The invention further relates to a pharmaceutically acceptable composition comprising a compound of formula (I) in the form of Mn(II) complex, or of a pharmaceutical salt thereof, in admixture with one or more physiologically excipients, diluents or solvents. Preferably, the pharmaceutical composition is a contrast-producing composition and, more preferably, a MRI contrast producing composition comprising at least one Mn(II) complex according to the invention.

In an additional aspect the invention relates to a MRI contrast medium comprising an effective amount of at least one compound according to the invention and, especially, of a Mn(II) complex with a compound of formula (I), or of a pharmaceutical acceptable salt thereof, in combination with one or more pharmaceutically acceptable excipients, diluents or solvents.

The selection of Mn(II) complex with a compound of formula (I) have a wide range of applications as they can be used for intravasal, (for instance intravenous, intraarterial, intracoronaric, intraventricular administration and the like), intrathecal, intraperitoneal, intralymphatic and intracavital administrations. Furthermore, they are suitable for the oral or parenteral administration and, therefore, specifically for the imaging of the gastrointestinal tract.

For instance, for parenteral administration they can be preferably formulated as sterile aqueous solutions or suspensions, whose pH can range from 6.0 to 8.5.

These formulations can be lyophilized and supplied as they are, to be reconstituted before use.

For the gastrointestinal use or for injection in the body cavities, these agents can be formulated as a solution or suspension optionally containing suitable excipients in order, for example, to control viscosity.

For the oral administration they can be formulated according to preparation methods routinely used in the pharmaceutical technique or as coated formulations to gain additional protection against the stomach acidic pH thus preventing, in case of chelated metal ions, their release which may take place particularly at the typical pH values of gastric fluids.

Other excipients, for example including sweeteners and/or flavouring agents, can also be added, according to known techniques of pharmaceutical formulations.

The solutions or suspensions of the compounds of this invention can also be formulated as aerosol to be used in aerosol-bronchography and instillation.

For example, they can be also encapsulated into liposomes or even constitute the liposomes themselves, as set forth above, and thus can be used as uni- or multi-lamellar vesicles.

In a preferred aspect, pharmaceutical compositions according to the invention are formulated in isotonic sterile aqueous, optionally buffered, solutions for parenteral administration, and most preferably for intravenous or intra-arterial administration.

More preferably, the said diagnostic composition has a concentration of Mn(II) complex with a compound of formula (I) of from 0.002 and 1.0 M and is supplied, for instance as a bolus, or as two or more doses separated in time, or as a constant or non-linear flow infusion.

In a further aspect, the invention relates to the use of a pharmaceutical composition including a Mn(II) complex compound formula (I) or pharmaceutical acceptable salt thereof for the diagnostic imaging, both in vitro (ex vivo) and in vivo, of pathological systems, including cells, biological fluids and biological tissues originating from a live mammal patient, and preferably, human patient, as well as of human body organ, regions or tissues, including tumors or cancerous tissues, inflammations, wherein fibrin deposition occurs as well as for monitoring the progress and results of therapeutic treatment of the said pathologies.

In an additional aspect, the present invention concerns a method for the in vivo imaging of a body organ, tissue or region by use of the MRI technique, said method comprising enhancing the signal generated by the water protons by use of a Mn(II) complex with a compound of formula (I) according to the invention, or a physiological acceptable salt thereof.

In one embodiment, said method comprises administering to a human or animal patient to be imaged a diagnostically effective amount of a composition of the invention comprising a compound of formula (I) in the form of complex with a Mn(II) ion then subjecting the administered patient to the diagnostic imaging by use of the MRI technique.

According to an embodiment of the invention, the above MRI method is performed on human or animal bodies suitably pre-administered with a diagnostically effective amount of a composition of the invention as above defined.

More particularly, according to an embodiment the present invention refers to a method for the in vivo imaging a human or animal body organ or tissue by use of the MRI technique that comprises the steps of:

a) submitting a human or animal pre-administered with a composition of the invention comprising a compound of formula (I) in the form of a Mn(II)-complex, or of a pharmaceutically acceptable salt thereof, and positioned in a MRI imaging system, to a radiation frequency selected to excite the non-zero proton spin nuclei of the active paramagnetic substrate; and b) recording a MR signal from said excited nuclei.

In yet another aspect the invention provides a method for the in vitro (ex vivo) imaging of biological samples, including cells, biological fluids and biological tissues originating from a live mammal patient, and preferably, human patient, by use of the MRI technique, that comprises contacting an effective amount of a Mn(II) complex compound of formula (I), or of a physiologically acceptable salt thereof, with the biological sample of interest and then obtaining MRI signals from said samples by use of the MRI technique.

Non-limiting examples of preferred compounds of the invention and intermediates for their preparation is reported in the following section, aimed to illustrate the invention in greater detail without limiting its scope.

EXPERIMENTAL PART

Example 1: Synthesis of CDTA-Dianhydride

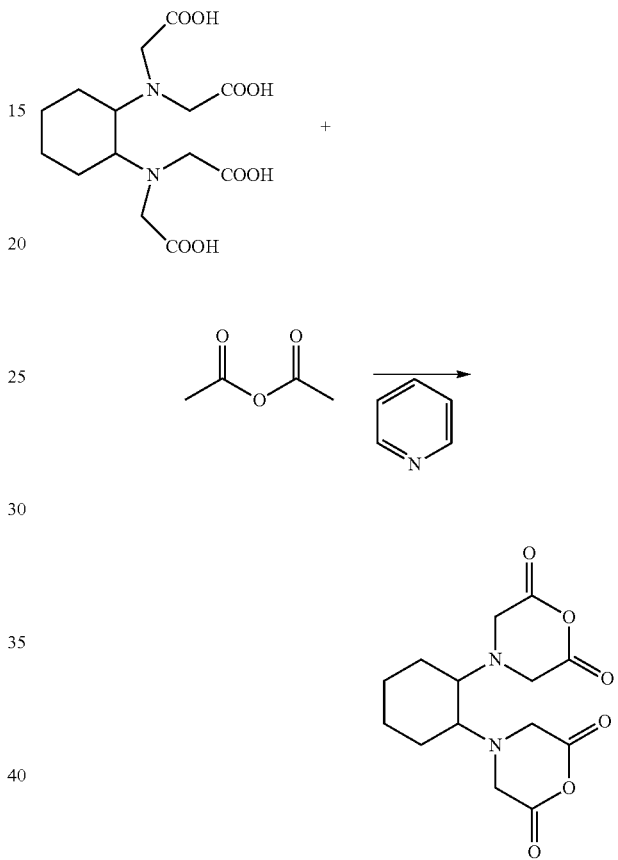

In detail, 12.00 g (0.0347 mol) of CDTA, 10.92 g (0.138 mol) of pyridine and 66.0 cm³ (71.28 g, 0.700 mol) of acetic anhydride are mixed under $N_2$ and stirred for 18 hours at room temperature. The reaction mixture is added dropwise to diethyl ether, the formed yellowish precipitate is vacuum filtered on a G3 glass frit and dried to constant weight.

Yield: 3.52 g (34%).

Melting point: T=214-218° C.;

$^1$H NMR [360 MHz, DMSO] δ 1.10 (4H, m, ($CH_2CH_2$) ring), 1.62 (4H, t, ($CHCH_2$) ring), 2.72 (2H, m, (CHCH) ring), 3.72 (8H, q, ($NCH_2$);

$^{13}$C NMR [100 MHz, DMSO] δ 24.1 (2C $CH_2$ ring); 26.7 (2C $CH_2$ ring); 48.4 (2C CH); 60.76 (4C NCH2); 165.7 (4C COO);

IR: 1768 cm$^{-1}$ (>C=O) and 1100 cm$^{-1}$ (≥C—O—C≤);

EA ($C_{14}H_{18}N_2O_6$*½ $CH_3COOH$): C, 52.29%; H, 6.14% and N, 8.60%) (expected: C, 52.94%; H, 5.92% and N, 8.23%).

Example 2: Preparation of Compound 2

Compound 2 is obtained by using the following synthetic procedure:

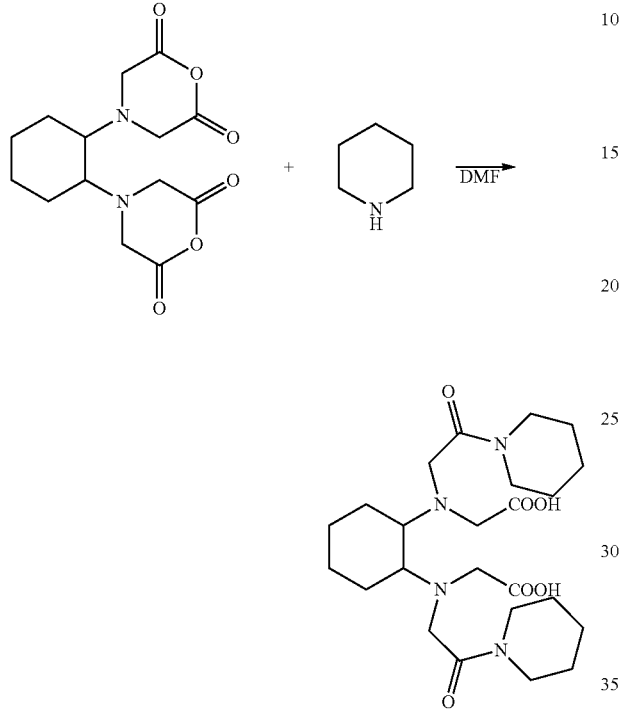

In detail, 0.264 g (0.000851 mol) of CDTA-dianhydride obtained in Example 1 and 0.29 g (0.00341 mol) of piperidine are mixed in 15 ml of dry DMF under $N_2$ and stirred for 18 hours at 50-60° C. The reaction mixture is concentrated under reduced pressure and the resulting brownish oil left to crystallize at 4° C. for 48 hours (the product may be precipitated by the addition of acetone, if crystallization does not occur). The crystals are vacuum filtered on a G3 glass frit, washed with 3×5 cm³ cold acetone and dried to constant weight. Yield: 0.16 g (39%).

Melting point: T=180-185° C.;

$^1$H NMR [360 MHz, $D_2O$, pD=12.5] δ 0.8-1.8 (18H, m, 4CH$_2$ ring, 6CH$_2$ piperidine), 2.3 (2H, d, CHCH), 2.7-3.9 (16H, m, 8H NCH$_2$, 8H NCH$_2$ piperidine);

$^{13}$C NMR [100 MHz, $D_2O$, pD=12.5] δ 27.5 (2C CH$_2$ ring), 28.9 (4C CH$_2$ piperidine), 29.2 (2C CH$_2$ ring), 29.7 (4C CH$_2$ piperidine), 47.2 (4C CH$_2$ piperidine), 49.8 (2C CON), 64.5 (2C COOH);

IR: 1634 cm$^{-1}$ (>C=O);

EA ($C_{24}H_{40}N_4O_6$*$H_2O$): C, 57.91%; H, 0.8.35% and N, 11.56%) (expected: C, 57.81%; H, 8.49% & N, 11.24%);

MS (ESI) m/z 481.300 (M+H)+35%; 503.282 (M+Na)+ 100%; 519.250 (M+K)+13%.

Example 3: Preparation of Compound 9

Compound 9 is obtained by using the following synthetic procedure:

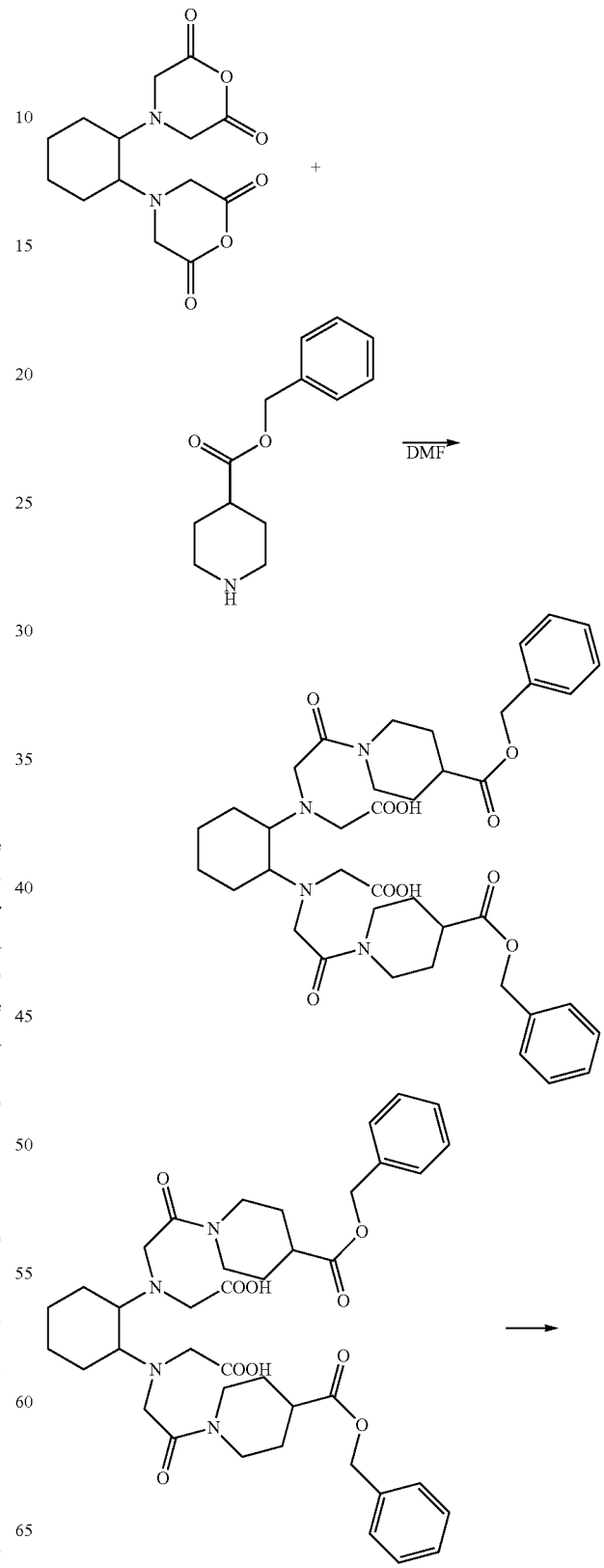

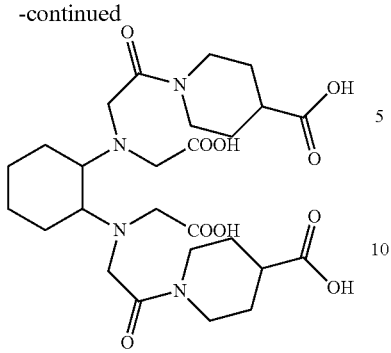

In detail, 0.5 g (0.00161 mol) of CDTA-dianhydride, synthesized in Example 1. step a.), is mixed with 1.06 g, (0.00483 mol, 3 eq.) of benzyl-(piperidine-4-carboxylic acid), synthesized in step a.) in 30 ml of dry DMF under $N_2$ and stirred for 18 hours at 50-60° C. The reaction mixture is concentrated under reduced pressure and the resulting brown oil is purified with HPLC. (column: Luna 10 u-Prep C18(2) 100 A (250×21.20 mm; 10 μm)), eluent:ACN:$H_2O$/0.005 M TFA. Yield: 0.46 g (38%).

Benzyl protecting groups are removed via catalytic hydrogenation. The benzyl-ester is dissolved in 60 $cm^3$ of methanol, argon is bubbled through the solution for 10 minutes and 0.0460 g (10%) of Pd/C catalyst is added. Hydrogenation took place at a pressure of 5 bar in a Parr apparatus for 24 hours at room temperature. The catalyst is filtered out, washed with methanol and the methanol filtrate is evaporated under reduced pressure, resulting in a white solid. Yield: 0.33 g (94%). Melting point: T=143-146° C.;

$^1$H NMR [400 MHz, $D_2O$] δ 1.0-1.2 (2H, m, $CH_2$ ring), 1.2-1.5 (4H, m, $CH_2CH_2$ ring), 1.6-1.9 (8H, m, 4CH piperidine), 1.9-2.1 (2H, m, $CH_2$ ring), 2.5 (2H, m, CHCOOH), 2.8-4.2 (18H, m, 4H $NCH_2CON$, 4H $NCH_2COOH$, 2H CHCOOH, 8H $CH_2$ piperidine);

$^{13}$C NMR [100 MHz, $D_2O$] δ 23.5 (2C $CH_2$ ring), 26.6 (2C $CH_2$ ring), 28.7 (4C $CH_2$ piperidine), 41.0 (4C, $CH_2$ piperidine), 41.5 (2C, CHCOOH), 52.7 (2C, $NCH_2CON$), 53.7 (2C, CH ring), 55.5 (2C, $NCH_2COOH$), 167.9 (2C, CON), 173.2 (2C, $CH_2COOH$), 180.0 (2C, CHCOOH;

IR: 3410 $cm^{-1}$ (COOH), 1720 & 1640 $cm^{-1}$ (>C=O);
MS (ESI) m/z 569.277 (M+H)+100%; 591.244 (M+Na)+ 20%; 607.223 (M+K)+25%.

Example 4: Preparation of Compound 12

Compound 12 is obtained by using the following synthetic procedure:

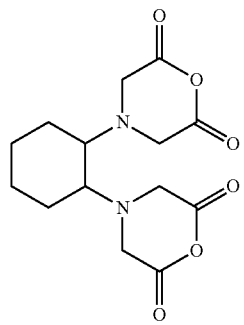 +

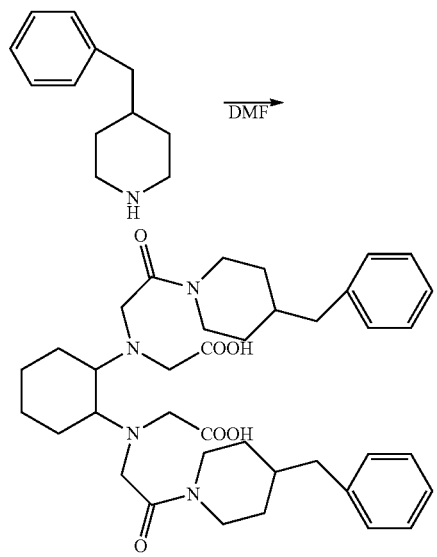

In detail, 1.0 g (0.00322 mol) of CDTA-dianhydride obtained in Example 1 and 2.26 g (0.0129 mol, 2.30 $cm^3$, 4 eq.) of 4-benzylpiperidine are mixed in 50 ml dry DMF under $N_2$ and stirred for 18 hours at 50-60° C. The reaction mixture is concentrated under reduced pressure and the resulting brownish oil is purified by HPLC: (YL9100 HPLC instrument equipped with column: Luna 10 u-Prep C18(2) 100 A (250×21.20 mm; 10 μm); 0-20% MeCN—H2O gradient elution), eluent:ACN:$H_2O$/TFA-t [ACN: acetonitrile; TFA: trifluoroacetic acid]. TFA is present at 0.005 M concentration in the water only. Yield: 1.02 g (48%).

Melting point: T=136-139° C.;

$^1$H NMR [360 MHz, $CH_3CN$] δ 1.1-1.9 (16H, m, 4$CH_2$ ring, 4$CH_2$ piperidine), 2.15 (2H, m, CHCH), 2.5-2.7 (6H, m, 2$CH_2$ benzyl, 2CH piperidine), 3.4-4.5 (16H, m, 8H $NCH_2$, 8H $NCH_2$ piperidine), 7.1-7.4 (10H, m, CH aromatic);

$^{13}$C NMR [100 MHz, $CH_3CN$] δ 27.5 (2C $CH_2$ ring), 28.0 (2C CH piperidine), 35.0 (2C $CH_2$ ring), 39.0 (4C, $CH_2$ piperidine), 41.5 (2C, $CH_2$ benzyl), 46.1 (4C, CH2 piperidine), 47.5 (2C, $NCH_2CON$), 48.5 (2C, $NCH_2COOH$), 66.5 (2C, CH ring) 129.6 (2C, CH aromatic), 132.0 (4C, CH aromatic); 132.8 (4C, CH aromatic), 144.2 (2C, C aromatic), 164.2 (2C, CON), 173.0 (2C, COOH);

IR: 3398 $cm^{-1}$ (COOH), 1734 $cm^{-1}$ (>C=O), 700 and 750 $cm^{-1}$ monosubstituted aromatic; 1644 $cm^{-1}$ (aromatic C=C);

MS (ESI) m/z 661.398 (M+H)+15%; 683.382 (M+Na)+ 100%; 705.362 (M+K)+25%.

Example 5: Preparation of Comparative Compound D

Comparative Compound D is obtained by using the following synthetic procedure:

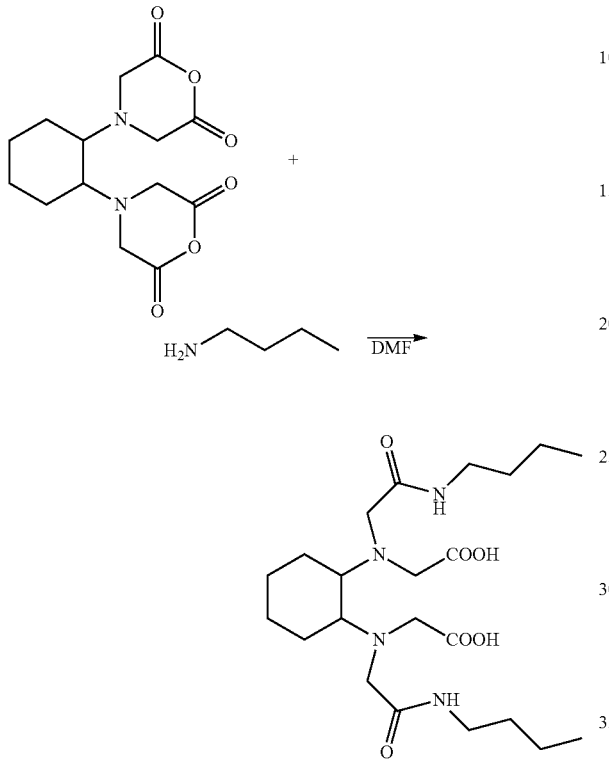

In detail, 2.28 g (0.00745 mol) of the CDTA-dianhydride obtained in Example 1 and 3.80 g (0.0520 mol) of butylamine are mixed in 90 ml of dry DMF under $N_2$ and stirred for 18 hours at 50-60° C. The reaction mixture is concentrated under reduced pressure and the resulting brownish oil left to crystallize at 4° C. for 48 hours (the product may be precipitated by the addition of acetone, if crystallization does not occur). The crystals are vacuum filtered on a G3 glass frit, washed with 3×30 cm³ acetone and dried to constant weight. Yield: 1.93 g (57%).

Melting point: T=158-162° C.;

$^1$H NMR [360 MHz, $D_2O$, pD=12.5] δ 0.87 (6H, t, $CH_3$), 1.09 (4H, broad, $CH_2$ butyl), 1.30 (4H, m, $CH_2$ butyl), 1.47 (4H, m, $CH_2CH_2$ ring), 1.66 (2H, broad, $CHCH_2$ ring), 1.94 (2H, broad, $CHCH_2$ ring), 2.43 (2H, broad, CH ring), 3.0-3.4 (12H, m, 8H $NCH_2CO$, 4H $CONHCH_2$)

$^{13}$C NMR [100 MHz, D2O, pD=12.5] δ 16.8 (2C $CH_3$); 22.3 (2C $CH_2$); 28.94 (2C $CH_2$ ring); 30.5 (2C $CH_2$ ring); 34.3 (2C $CH_2$); 42.6 (2C $CH_2$); 58.8 (2C $NCH_2COOH$); 59.3 (2C $NCH_2CO$); 65.2 (2C CH); 178.7 (2C CONH); 184.0 (2C COOH);

IR: 1644 cm$^{-1}$ (>C=O) & 3078 cm$^{-1}$ (>NH);

EA ($C_{22}H_{40}N_4O_6$*$H_2O$): C, 56.07%; H, 8.83% and N, 11.90%) (expected: C, 55.68%; H, 8.83% & N, 11.90%);

MS (ESI) m/z 457.299 (M+H)+50%; 479.281 (M+Na)+ 100%; 495.250 (M+K)+13%.

Example 6: Synthesis of PhDTA-Dianhydride a.) Synthesis of PhDTA:

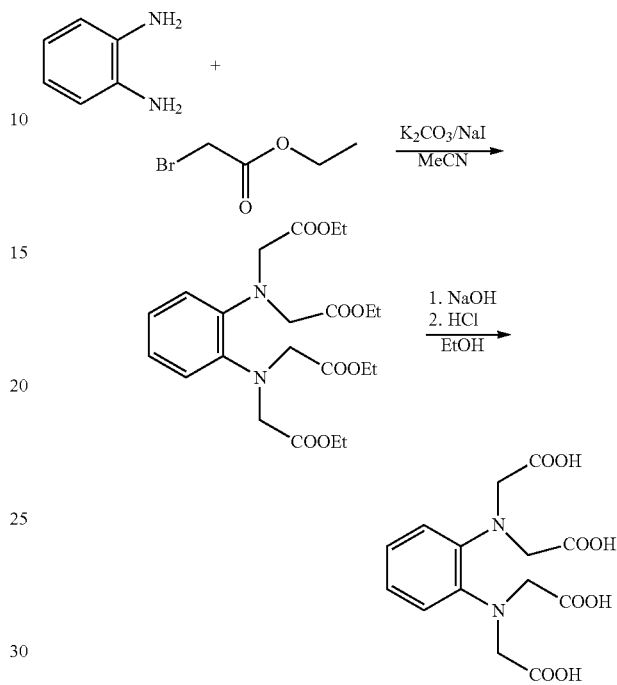

In detail, 1.10 g (0.0102 mol) of 1,2-diaminobenzene, 6.70 cm³ (10.1 g, 0.0605 mol) of ethyl-bromoacetate, 1.30 g (0.00867 mol) of sodium iodide and 8.30 cm³ (6.16 g, 0.0477 mol) of diisopropyl-ethylamine are mixed in 10 cm³ of acetonitrile under $N_2$ and refluxed for 7 hours. The reaction mixture is cooled to room temperature and concentrated under reduced pressure, redissolved in 50 cm³ of water and extracted with 3×40 cm³ of chloroform. The organic phases are combined, dried over $Na_2SO_4$, and concentrated under reduced pressure. The resulting brownish oil is purified with flash chromatography: (column: $SiO_2$, eluent: 10:1 v/v petroleum ether:ethyl-acetate).

Yield: 2.90 g (62%).

2.90 g (0.00641 mol) of PhDTA-tetra(ethyl)-ester is dissolved in 40 cm³ of ethanol and a solution of 1.28 g of NaOH (0.0320 mol) made with 5 cm³ of water is added dropwise. The addition of NaOH causes the immediate formation of white precipitate, however the reaction mixture is refluxed for 18 hours to achieve better yield. The crystalline white product is vacuum filtered on a G3 glass frit, redissolved in 2-3 cm³ water and the pH is set with cc. HCl to pH=0-1. The precipitated white substance (acid form of PhDTA) is again vacuum filtered on a G3 glass frit, washed with 3×5 cm³ cold water and dried to constant weight.

Yield: 1.78 g (52%).

$^1$H NMR [360 MHz, $D_2O$] δ 4.05 (8H, s, $NCH_2$), 7.2-7.4 (4H, m, CHCH aromatic);

$^{13}$C NMR [100 MHz, $D_2O$] δ 57.7 (4C $NCH_2$), 123.2 (2C CH ring), 127.6 (2C CH ring), 141.0 (2C C ring), 174.7 (4C CO);

MS (ESI) m/z 481.300 (M+H)+35%; 503.282 (M+Na)+ 100%; 519.250 (M+K)+13%.

b.) Synthesis of PhDTA-Dianhydride:

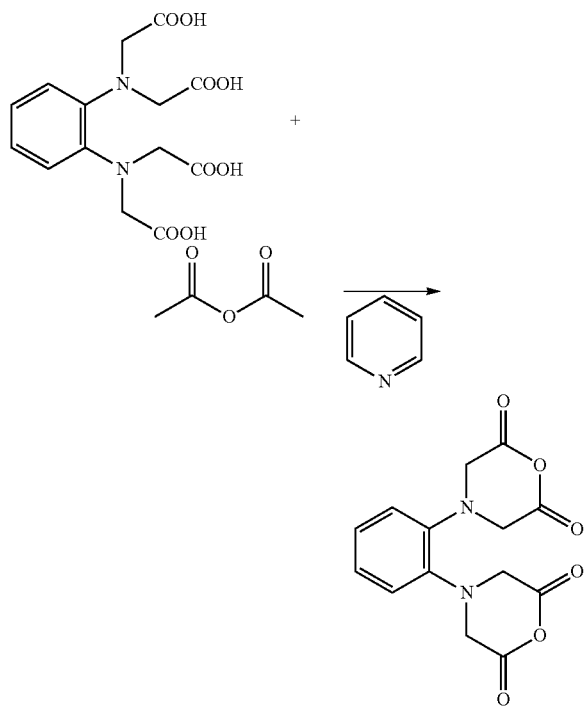

0.45 g (0.00132 mol) of PhDTA, 0.411 g (0.420 ml, 0.00520 mol) of pyridine and 7.50 ml (8.10 g, 0.0793 mol) of acetic anhydride are mixed under $N_2$ and stirred for 18 hours at room temperature. The reaction mixture is added dropwise to diethyl ether, the formed white precipitate is vacuum filtered on a G3 glass frit and dried to constant weight.

Yield: 0.26 g (65%).

$^1$H NMR [360 MHz, DMSO] δ 4.29 (8H, s, $NCH_2$), 6.41 (4H, s, CHCH aromatic);

$^{13}$C NMR [100 MHz, DMSO] δ 61.3 (4C $NCH_2$), 115.2 (2C CH ring), 119.2 (2C CH ring), 135.6 (2C C ring), 166.0 (4C CO).

Example 7: Preparation of Comparative Compound E

Comparative Compound E (is obtained by using the following synthetic procedure:

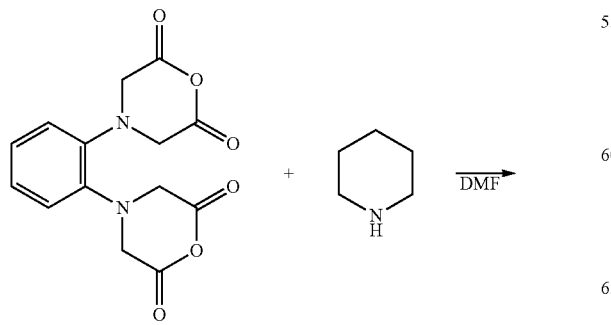

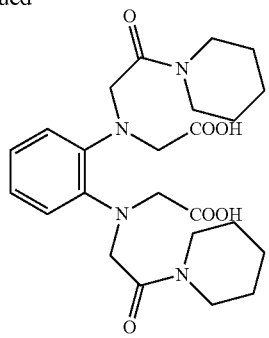

In detail 0.26 g (0.000854 mol) of PhDTA-dianhydride obtained in Example 6, step b.) and 0.29 g (0.00341 mol) of piperidine are mixed in 5 cm$^3$ of dry DMF, under $N_2$ and stirred for 18 hours at 50-60° C. The resulting white precipitate is filtered on a G3 glass frit and redissolved in 3 cm$^3$ of distilled water. White precipitation occurs when pH is set to 4-5 with concentrated hydrochloric acid, which is filtered once more (on a G3 glass frit), washed with 3×3 cm$^3$ cold distilled water and dried to constant weight under vacuum.

Yield: 0.19 g (47%).

$^1$H NMR [360 MHz, $D_2O$] δ 1.1-1.5 (12H, m, $CH_2$ piperidine), 3.2 (8H, m, $NCH_2$ piperidine), 3.85 (4H, s, $CH_2CON$), 4.4 (4H, s, $CH_2COOH$), 6.7-6.9 (4H, m, (CH aromatic);

$^{13}$C NMR [100 MHz, $D_2O$] δ 25.4 (4C $CH_2$ piperidine), 25.6 (2C $CH_2$ piperidine), 44.5 (2C $CH_2$ piperidine), 57.5 (2C $NCH_2CO$), 59.6 (2C $NCH_2COOH$), 115.2 (2C CH aromatic), 119.2 (2C CHCH aromatic), 135.8 (2C, C aromatic), 167.9 (2C CON), 173.2 (2C COOH).

Example 8: Preparation of Comparative Compound F

Comparative Compound F is obtained by using the following synthetic procedure:

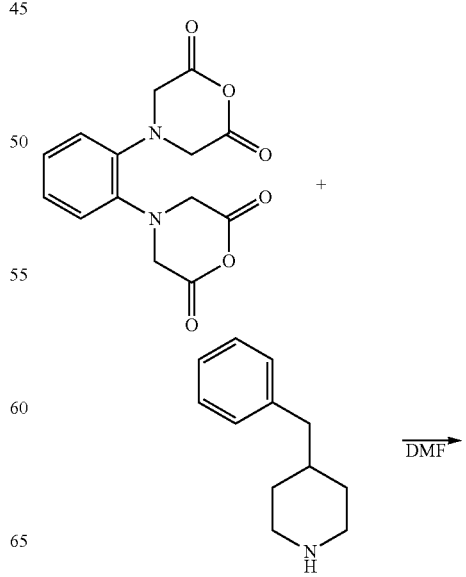

-continued

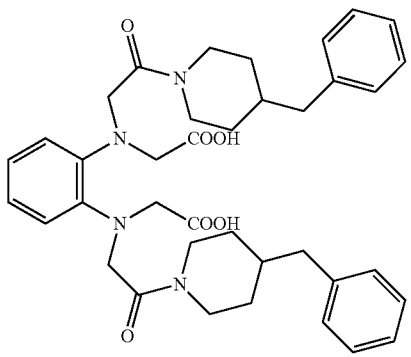

In detail, 0.42 g (0.00138 mol) of PhDTA-dianhydride, synthesized in Example 6, step b.) and 0.97 g (0.00552 mol) of 4-benzylpiperidine are mixed in 25 cm³ of dry DMF under $N_2$, and stirred for 18 hours at 50-60° C. The solvent is evaporated under reduced pressure and the product is purified with HPLC (YL9100 HPLC instrument equipped with column: Luna 10 u-Prep C18(2) 100 A (250×21.20 mm; 10 μm); 0-20% MeCN—$H_2O$ gradient elution), eluent: ACN:H2O/0.005 M TFA. Yield: 0.3 g (33%).

Melting point: T=96-100° C.;

$^1$H NMR [360 MHz, $CH_3CN$] δ 1.1-1.3 (4H, m, $CH_2$ piperidine), 1.6 (4H, m, $NCH_2$ piperidine), 1.8 (2H, m, CHCH ring), 2.6 (4H, d, $CH_2$ benzyl), 3.4 (8H, m, $CH_2$ piperidine), 4.3 (8H, m, 4H $NCH_2CON$, 4H $NCH_2COOH$), 7.1-7.6 (14H, m CH aromatic);

$^{13}$C NMR [100 MHz, $D_2O$] δ 24.2 (2C CH piperidine), 29.4 (4C $CH_2$ piperidine), 40.7 (2C $CH_2$ benzyl), 42.3 (4C $CH_2$ piperidine), 57.5 (2C $NCH_2CO$), 59.3 (2C $NCH_2COOH$), 115.2 (2C CH aromatic), 119.2 (2C CHCH aromatic), 126.0 (2C CH aromatic), 128.2 (4C CH aromatic), 135.4 (2C, C aromatic), 138.7 (2C CH aromatic), 167.6 (2C CON), 173.2 (2C COOH);

IR: 3404 cm$^{-1}$ (COOH), 1734 cm$^{-1}$ (>C=O), 700 & 746 cm$^{-1}$ aromatic monosubstituted; 1636 cm$^{-1}$ (aromatic C=C).

Example 9: Complexation of the Chelating Compounds

The synthesis of Mn(II) complexes requires the use of manganese(II) salts with anions tolerable to the human body (chloride, sulfate, acetate, etc.) Use of $MnCl_2$ is the simplest solution, though the increase of chloride concentration by at least 2 equivalents per molecule, needs to be calculated with. From a medical viewpoint however, reacting MnO or $MnCO_3$ with the acid form of the ligand is the most favorable, as the only byproducts are water and $CO_2$.

During the synthesis of Mn(II) complexes, it is practical to use 1:1 molar ratio. Ligands and Mn(II) were mixed in 1:1 ratio in concentrations ranging between 0.001-0.05 mol/dm³ at pH 6-8 throughout the laboratory examination of Mn(II) complexes. This range may be expanded, it is both possible to synthesize the complexes on a micromolar scale and to raise concentrations into the 0.1-1.0 mol/dm³ range. The upper limit is of course defined by the solubility of the individual complexes. When choosing the applied concentrations however, the relaxation properties of the complexes must also be considered, as high-relaxivity complexes may allow the use of lower concentration solutions.

Results

The relaxivity values $r_1$ obtained from some representative compounds according to the invention, in water, both in absence and presence of human serum albumin (HSA), at 25 and 37° C., at 20 MHz, are summarized in the following Table 1, together with the structure of tested compounds, and compared with corresponding values measured for some Comparative Compounds.

TABLE 1

(relaxivity values $r_1$)

| Complex | T (° C.) | $r_1$ (mM$^{-1}$s$^{-1}$) | $r_1$ (mM$^{-1}$s$^{-1}$) HSA |
|---|---|---|---|
| | 25 | 4.43 | 5.63 |
| | 37 | 3.49 | 4.56 |

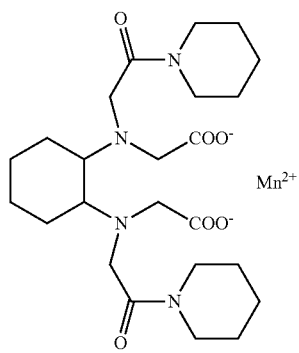

Compound 2 Mn(II) complex

TABLE 1-continued
| | (relaxivity values $r_1$) | | |
|---|---|---|---|
| Complex | T (° C.) | $r_1$ (mM$^{-1}$s$^{-1}$) | $r_1$ (mM$^{-1}$s$^{-1}$) HSA |
| | 25 | 4.97 | 5.98 |
| | 37 | 3.75 | 4.65 |
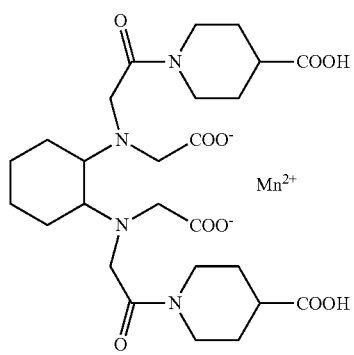
Compound 9 Mn(II) complex
| | 25 | 5.56 | 19.44 |
|---|---|---|---|
| | 37 | 4.17 | 18.16 |
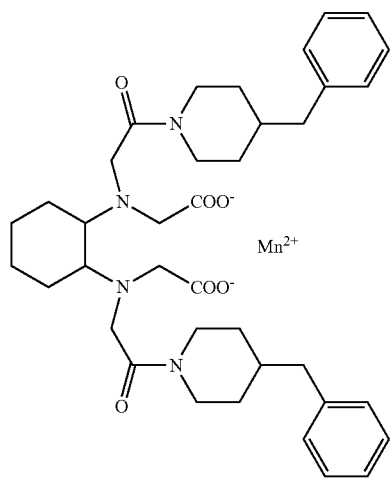
Compound 12 Mn(II) complex
| | 25 | 3.77 | 7.64 |
|---|---|---|---|
| | 37 | 2.95 | 6.57 |
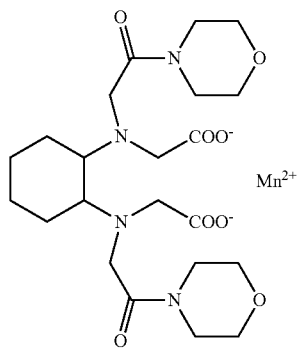
Compound A Mn(II) complex
(Comparative, Ex. 4 in US 5,693,310)

TABLE 1-continued (relaxivity values $r_1$)

| Complex | T (° C.) | $r_1$ (mM$^{-1}$s$^{-1}$) | $r_1$ (mM$^{-1}$s$^{-1}$) HSA |
|---|---|---|---|
| Compound B Mn(II) complex (Comparative, Ex. 7 in US 5,419,894) | 25<br>37 | 5.17<br>3.94 | 6.01<br>4.44 |
| Compound C Mn(II) complex (Comparative, Ex. 11 in US 5,693,310) | 25<br>37 | 4.37<br>3.43 | 13.10<br>9.94 |
| Compound D Mn(II) complex (Comparative) | 25<br>37 | 4.64<br>3.62 | 6.55<br>5.37 |
| Compound E Mn(II) complex (Comparative) | 25<br>37 | 4.60<br>3.50 | 9.09<br>6.78 |

TABLE 1-continued (relaxivity values $r_1$)

| Complex | T (°C.) | $r_1$ (mM$^{-1}$s$^{-1}$) | $r_1$ (mM$^{-1}$s$^{-1}$) HSA |
|---|---|---|---|
| Compound F Mn(II) complex (Comparative) | 25 | 5.29 | 28.20 |
|  | 37 | 4.04 | 23.84 |

The half-lives of some representative compounds according to the invention, calculated using the rate constants characterizing the decomplexation of the Mn(II) complexes at 25° C. and pH=7.4, are summarized in the following Table 2, together with the structure of tested compounds, and compared with corresponding values measured for some Comparative Compounds. These studies were performed by following the transmetallation reaction between the Mn$^{2+}$ based complexes and Cu$^{2+}$ ions by spectrophotometry as reported in Kalman, F. K.; Tircsó, G. Inorganic Chemistry (2012), 51, 10065-7.

TABLE 2

(half-lives)

| Complex | t½ (h) |
|---|---|
| Mn(II) complex of Compound 2 (R,R) | 285 |
| Mn (II) complex of Compound 2 (R,S) | 541 |
| Mn(II) complex of Compound 9 (R,R) | 123 |

TABLE 2-continued (half-lives)

| Complex | t½ (h) |
|---|---|
| Mn(II) complex of Compound 9 (R,S) | 948 |
| Mn(II) complex of Compound 12 (R,R) | 115 |
| Mn(II) complex of Compound 12 (R,S) | 653 |
| Mn(II) complex of Comparative Compound A (R,R) | 16 |
| Mn(II) complex of Comparative Compound A (R,S) | 201 |
| Mn(II) complex of Comparative Compound B | 166 |

TABLE 2-continued (half-lives)

| Complex | t½ (h) |
|---|---|
| Mn(II) complex of Comparative Compound C | 131 |
| Mn(II) complex of Comparative Compound D | 57 |
| Mn(II) complex of Comparative Compound E | (83)* |
| Mn(II) complex of Comparative Compound F | (60)* |

*= half-life in seconds

These results confirm that the particular selection represented by the Mn(II) complexes of the compounds of formula (I) of the invention show an increased kinetic inertness, which is at least 2 times the kinetic inertness shown, at the same conditions, by the contrast agents known in the art.

The invention claimed is:

1. A compound of formula (I)

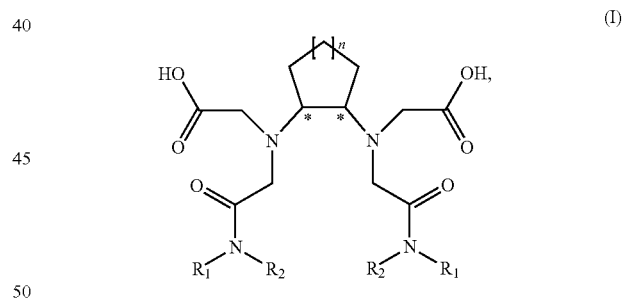

(I)

wherein:
n is 1, 2 or 3; and
wherein:
R$_1$ and R$_2$, taken together with the adjacent N atom, form a 5-6 membered unsubstituted aromatic ring;
or
R$_1$ and R$_2$, taken together with the adjacent N atom, form a 6-7 membered unsubstituted saturated ring;
or
R$_1$ and R$_2$, taken together with the adjacent N atom, form a 5-7 membered saturated ring substituted (i) by one or more hydroxyls and by one additional group selected from the group consisting of alkyl, hydroxyalkyl, and cycloalkyl-alkyl; or (ii) by acyl or aminocarbonyl substituted at the aminocarbonyl nitrogen by polyhydroxyalkyl, Ar, or —Y—Ar, wherein Y is a moiety selected from the group consisting of alkyl, acyl, and carbamoyl and Ar is aryl optionally substituted;

or $R_1$ and $R_2$, taken together with the adjacent N atom, form a 6 membered heterocycloalkyl ring with a heteroatom other than the adjacent N atom and substituted at the heteroatom by —Y—Ar wherein Y and Ar are as defined above;

or $R_1$ and $R_2$, taken together with the adjacent N atom, form a 10 or 11 membered saturated spiro bicyclic ring, optionally containing O as an additional heteroatom other than the adjacent N atom and optionally substituted;

or $R_1$ and $R_2$, taken together with the adjacent N atom, form a 8-membered bridged ring optionally substituted by one or two hydroxyl moieties.

2. The compound according to claim 1, wherein n is 2.

3. The compound according to claim 1, wherein $R_1$ and $R_2$, taken together with the adjacent N atom, form a 5 membered unsubstituted aromatic ring.

4. The compound according to claim 1, wherein $R_1$ and $R_2$, taken together with the adjacent N atom, form a 6-7 membered unsubstituted saturated ring.

5. The compound according to claim 1, wherein $R_1$ and $R_2$, taken together with the adjacent N atom, form a 6 membered saturated ring substituted by one hydroxyl and one additional moiety selected from the group consisting of methyl, hydroxymethyl, cyclopentylmethylene, and cyclohexylmethylene.

6. The compound according to claim 5, wherein the methyl or hydroxymethyl moiety is at an ortho position and the hydroxyl moiety is at a meta position.

7. The compound according to claim 5, wherein the methyl or hydroxymethyl moiety is at a meta position and the hydroxyl moiety is at the other meta position or at the para position.

8. The compound according to claim 1, wherein $R_1$ and $R_2$, taken together with the adjacent N atom, form a 5-6 membered saturated ring substituted by a carboxyl moiety.

9. The compound according to claim 8, wherein the carboxyl is at a meta or the para position.

10. The compound according to claim 1, wherein $R_1$ and $R_2$, taken together with the adjacent N atom, form a 6 membered saturated ring substituted by an aminocarbonyl moiety which is in turn substituted at the aminocarbonyl nitrogen by bis(hydroxymethyl)methyl [—CH(CH$_2$OH)$_2$], 2,3,4,5,6-hydroxyhexyl [—CH$_2$—CH(OH)—CH(OH)—CH(OH)—CH(OH)—CH$_2$(OH)], or 2,3-hydroxypropyl [—CH$_2$—CH(OH)—CH$_2$(OH)].

11. The compound according to claim 10, wherein the aminocarbonyl moiety on the saturated ring is at the para position.

12. The compound according to claim 1, wherein $R_1$ and $R_2$, taken together with the adjacent N atom, form a 6 membered saturated ring substituted by a phenyl residue optionally substituted by one or two hydroxyl moieties or by one moiety selected from the group consisting of nitro, amino, sulphonic, and hydroxymethyl.

13. The compound according to claim 12, wherein the phenyl moiety on the saturated ring is at the para position and said phenyl moiety is substituted by two hydroxyl moieties at both ortho positions or by one group selected from the group consisting of nitro, amino, sulphonic, and hydroxymethyl at the para position.

14. The compound according to claim 1, wherein $R_1$ and $R_2$, taken together with the adjacent N atom, form a 6 membered saturated ring substituted by —Y—Ar wherein Y is methylene (—CH$_2$—), carbonyl (—CO—), or aminocarbonyl (—CO—NH—) and Ar is phenyl.

15. The compound according to claim 14, wherein Y is methylene and the phenyl residue is optionally substituted by one or two hydroxyl or by one group selected from the group consisting of nitro, amino, sulphonic, and hydroxymethyl.

16. The compound according to claim 15, wherein the phenylmethylene on the saturated ring is at the para position with respect to the N of the saturated ring and two hydroxyl moieties on the phenyl are at both ortho positions.

17. The compound according to claim 15, wherein the phenylmethylene on the saturated ring is at the para position and said phenylmethylene moiety is substituted by one group selected from the group consisting of nitro, amino, sulphonic, and hydroxymethyl at the para position.

18. The compound according to claim 14, wherein Y is carbonyl and the phenyl residue is substituted by one or two hydroxyl.

19. The compound according to claim 14, wherein Y is aminocarbonyl and the phenyl residue is substituted by one or two hydroxyl or by one hydroxyalkyl.

20. The compound according to claim 19, wherein the phenylaminocarbonyl on the saturated ring is at an ortho or the para position and wherein said phenylaminocarbonyl moiety is substituted by two hydroxyls, one at an ortho and the other at the para position with respect to the C linked to the aminocarbonyl group or both at ortho positions, or by one hydroxyl or hydroxyalkyl at the para position.

21. The compound according to claim 1, wherein $R_1$ and $R_2$, taken together with the adjacent N atom, form a 6 membered heterocycloalkyl ring comprising a second N atom, said second N atom being substituted by a sulphonic group or by —Y—Ar wherein Y is carbonyl and Ar is phenyl substituted by one or two hydroxyl moieties.

22. The compound according to claim 21, wherein the second N atom on the 6 membered heterocycloalkyl ring is at the para position with respect to the adjacent N atom and the two hydroxyl moieties on the phenyl are one at an ortho position and the other at the para position or both at ortho positions.

23. The compound according to claim 1, selected from the group consisting of:

Compound 1

Compound 2
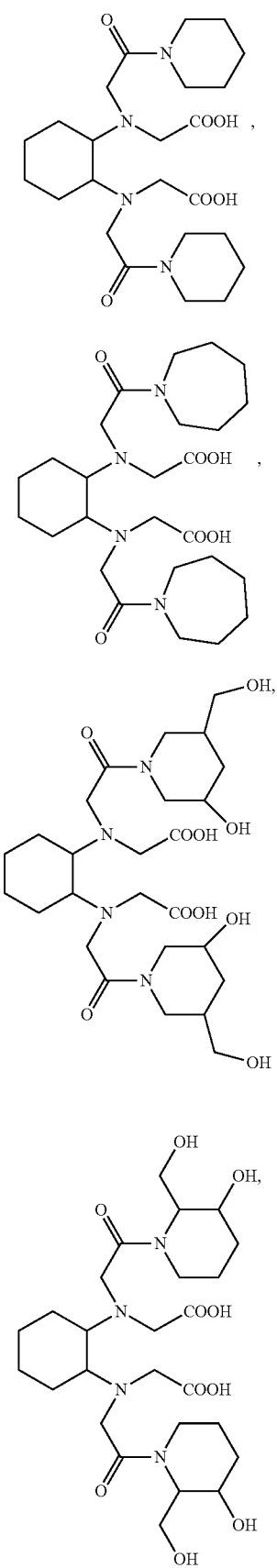
Compound 3
Compound 4
Compound 5
Compound 6
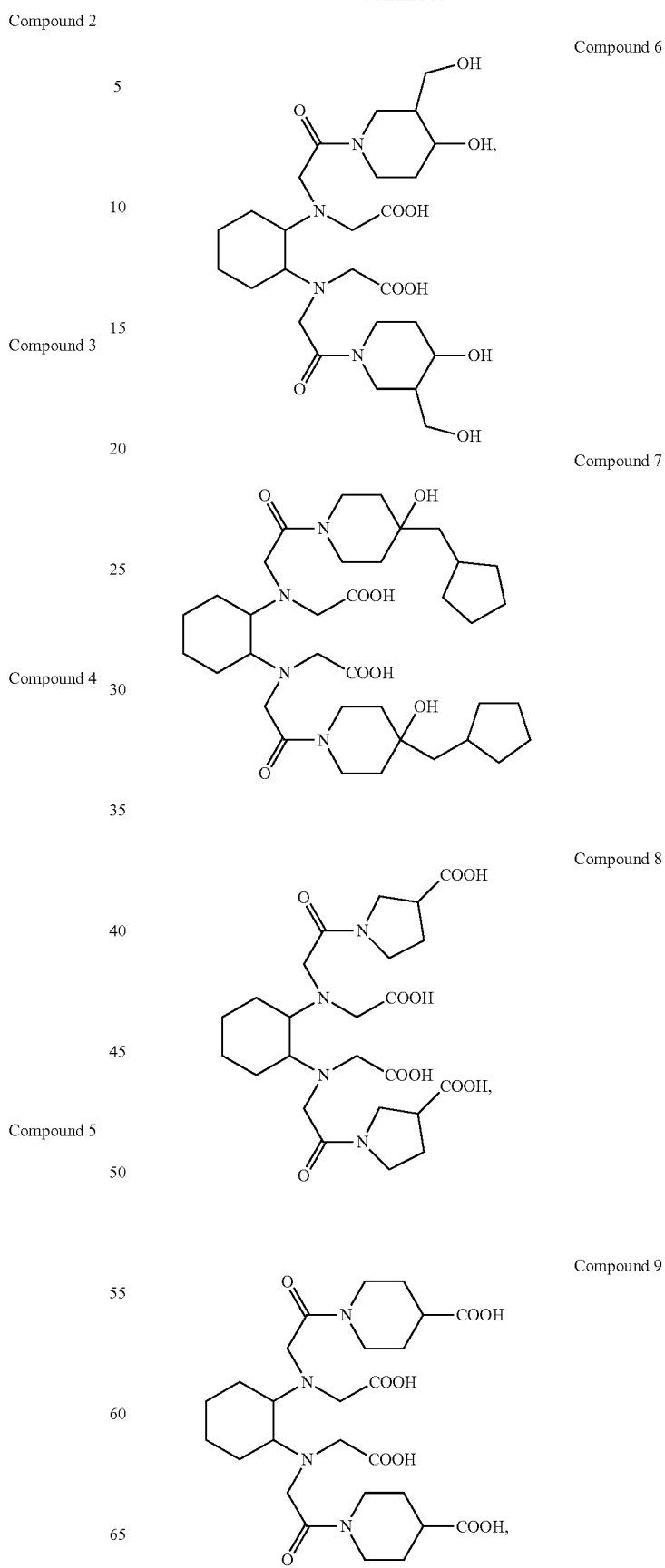
Compound 7
Compound 8
Compound 9

Compound 10
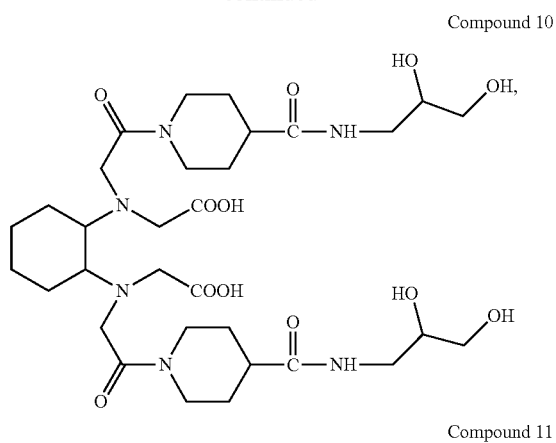
Compound 11
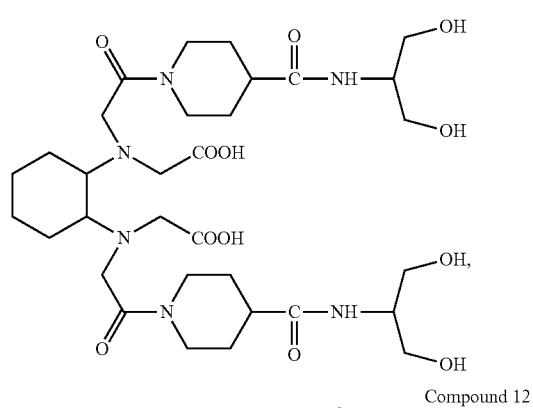
Compound 12
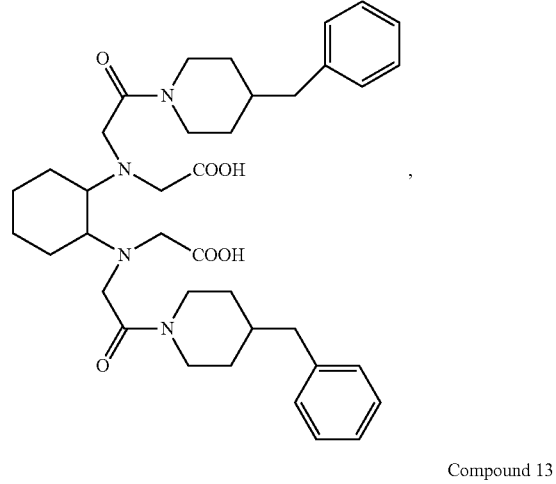
Compound 13
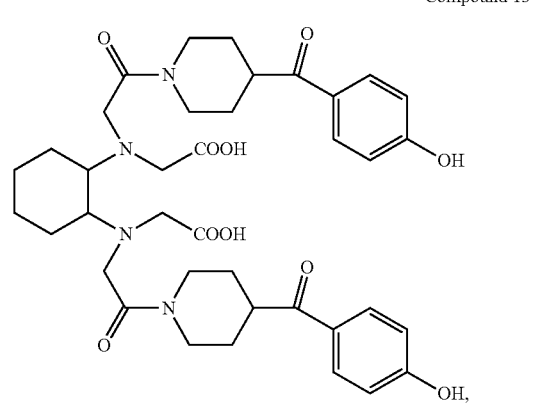
Compound 14
Compound 15
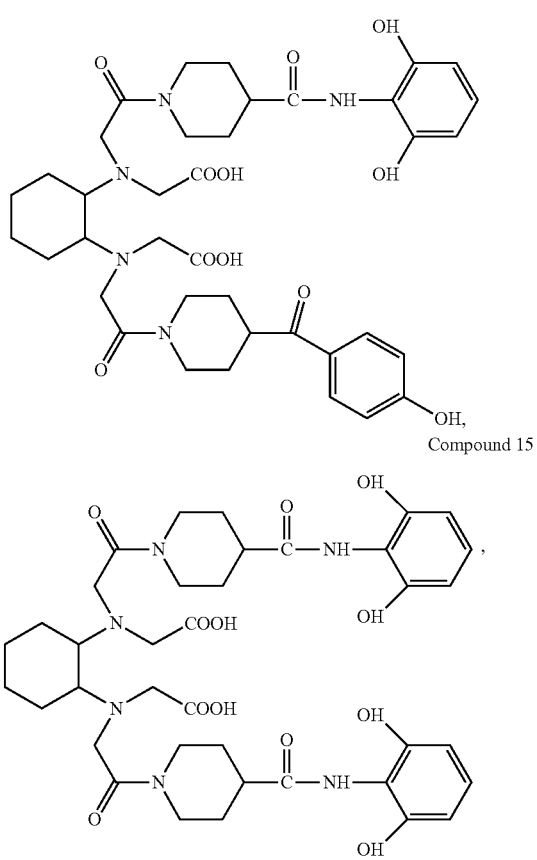
Compound 16
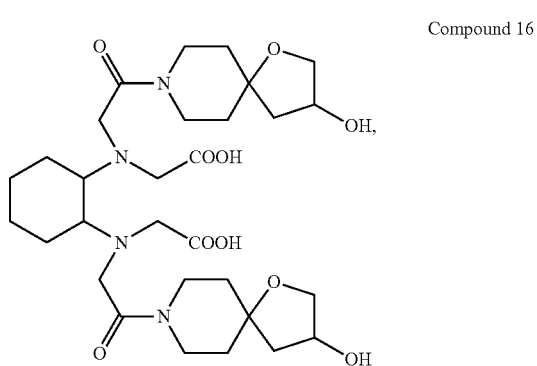
Compound 17
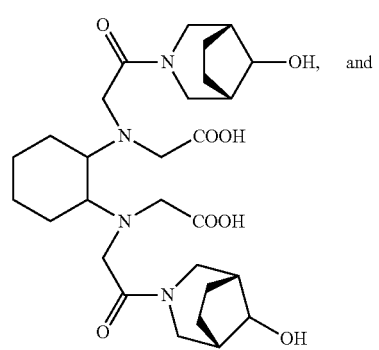
and Compound 18

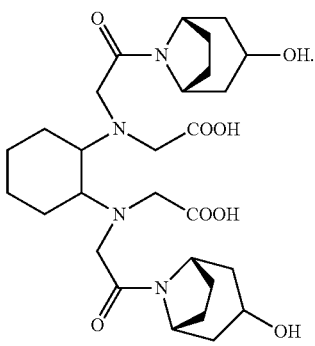

24. The compound as defined in claim 23, wherein Compound 2, Compound 9, and Compound 12 are in the R,S diastereoisomeric form.

25. The compound of formula (I) according to claim 1 in a form of a complex with a Mn(II) ion, or a physiologically acceptable salt thereof.

26. The compound of formula (I) as defined in claim 1 for use as an MRI contrast agent.

27. A pharmaceutical composition comprising the compound of formula (I) as defined in claim 1 in a form of Mn(II) complex, or a pharmaceutical salt thereof, in combination with one or more pharmaceutically acceptable carriers, diluents, or excipients.

28. A process for a preparation of the compound of formula (I) as defined in claim 25 comprising the following main steps:

a) synthesizing CDTA-dianhydride;
b) carrying out an opening reaction of the CDTA-dianhydride in the presence of a secondary amine to give the corresponding bisamide;
c) carrying out a complexation of the obtained bisamide with a Mn(II) ion and isolation of the Mn(II) complex, or the salt thereof.

29. A method for an in vivo imaging of a human or animal body organ, tissue or region by use of an MRI technique that comprises the steps of:

a) submitting a human or animal pre-administered with a composition comprising the compound of claim 1 in a form of a paramagnetic complex with a Mn(II) ion, or a pharmaceutically acceptable salt thereof, and positioned in an MRI imaging system, to a radiation frequency selected to excite non-zero proton spin nuclei of an active paramagnetic substrate; and
b) recording a MR signal from said excited nuclei.

30. A method for an in vitro (ex vivo) imaging of a biological sample originating from a live mammal patient, by use of an MRI technique, that comprises contacting an effective amount of a Mn(II) complexed with the compound of claim 1, or a physiologically acceptable salt thereof with the biological sample of interest and then obtaining MRI signals from said sample by use of the MRI technique.

31. The method for an in vitro (ex vivo) imaging according to claim 30, wherein the biological sample is selected from the group consisting of cells, biological fluids and biological tissues.

32. The method for an in vitro (ex vivo) imaging according to claim 30, wherein the live mammal patient is a human patient.

* * * * *